United States Patent [19]

Yoshizaki et al.

[11] 4,223,137
[45] Sep. 16, 1980

[54] CARBOSTYRIL DERIVATIVES AND PROCESS FOR PREPARING THE SAME

[75] Inventors: Shiro Yoshizaki; Shigeharu Tamada; Eiyu Yo; Kazuyuki Nakagawa, all of Tokushima, Japan

[73] Assignee: Otsuka Pharmaceutical Co., Ltd., Tokyo, Japan

[21] Appl. No.: 932,572

[22] Filed: Aug. 10, 1978

Related U.S. Application Data

[63] Continuation of Ser. No. 756,651, Jan. 4, 1977, abandoned.

[30] Foreign Application Priority Data

Oct. 8, 1976 [JP] Japan .................. 51/121423

[51] Int. Cl.² .................. C07D 215/26; C07D 215/32
[52] U.S. Cl. .................. 544/128; 424/248.56; 424/250; 424/258; 544/363; 546/157; 546/158
[58] Field of Search .................. 546/157, 158; 544/128, 544/363

[56] References Cited

U.S. PATENT DOCUMENTS

| | | |
|---|---|---|
| 3,975,391 | 8/1976 | Nakagawa et al. .............. 546/157 X |
| 3,994,901 | 11/1976 | Nakagawa et al. .............. 546/158 OR |
| 4,022,776 | 5/1977 | Nakagawa et al. .............. 546/157 X |
| 4,022,784 | 5/1977 | Nakagawa et al. .............. 546/158 X |
| 4,026,897 | 5/1977 | Nakagawa et al. .............. 546/157 OR |
| 4,072,683 | 2/1978 | Nakagawa et al. .............. 546/158 OR |

FOREIGN PATENT DOCUMENTS 823841 1/1975 Belgium .................. 546/157

*Primary Examiner*—John D. Randolph
*Attorney, Agent, or Firm*—Sughrue, Rothwell, Mion, Zinn and Macpeak

[57] ABSTRACT

Carbostyril derivative represented by the formula (I):

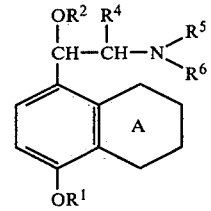

wherein $R^1$ and $R^2$, which may be the same or different, each represents a hydrogen atom, a cycloalkylcarbonyl group, a cycloalkylalkanoyl group, a benzoyl group, an alkanoyl group or a phenylalkylcarbonyl group; $R^4$ represents a hydrogen atom or an alkyl group, $R^5$ and $R^6$, which may be the same or different, each represents a hydrogen atom, an alkyl group, a cycloalkyl group, or a phenylalkyl group, or $R^5$ and $R^6$ may, when taken together with the nitrogen atom to which they are attached, form a 5- or 6-membered substituted or unsubstituted heterocyclic ring containing 1 or 2 nitrogen or oxygen atoms as hetero atoms; and the ring A has a partial structure:

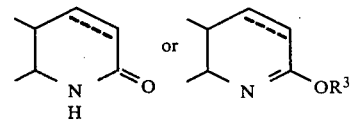

wherein $R^3$ represents a hydrogen atom, a cycloalkylcarbonyl group, a cycloalkylalkanoyl group, a benzoyl group, an alkanoyl group or a phenylalkylcarbonyl group, with the proviso that at least one of $R^1$, $R^2$ and $R^3$ when $R_3$ is present, or at least one of $R_1$ and $R_2$ when $R_3$ is absent, represents a cycloalkylcarbonyl group, a cycloalkylalkanoyl group, a benzoyl group, an alkanoyl group or a phenylalkylcarbonyl group; the pharmaceutically acceptable acid addition salts of the above carbostyril compounds represented by the formula (I), and processes for preparing the above carbostyril compounds represented by the formula (I).

38 Claims, 1 Drawing Figure

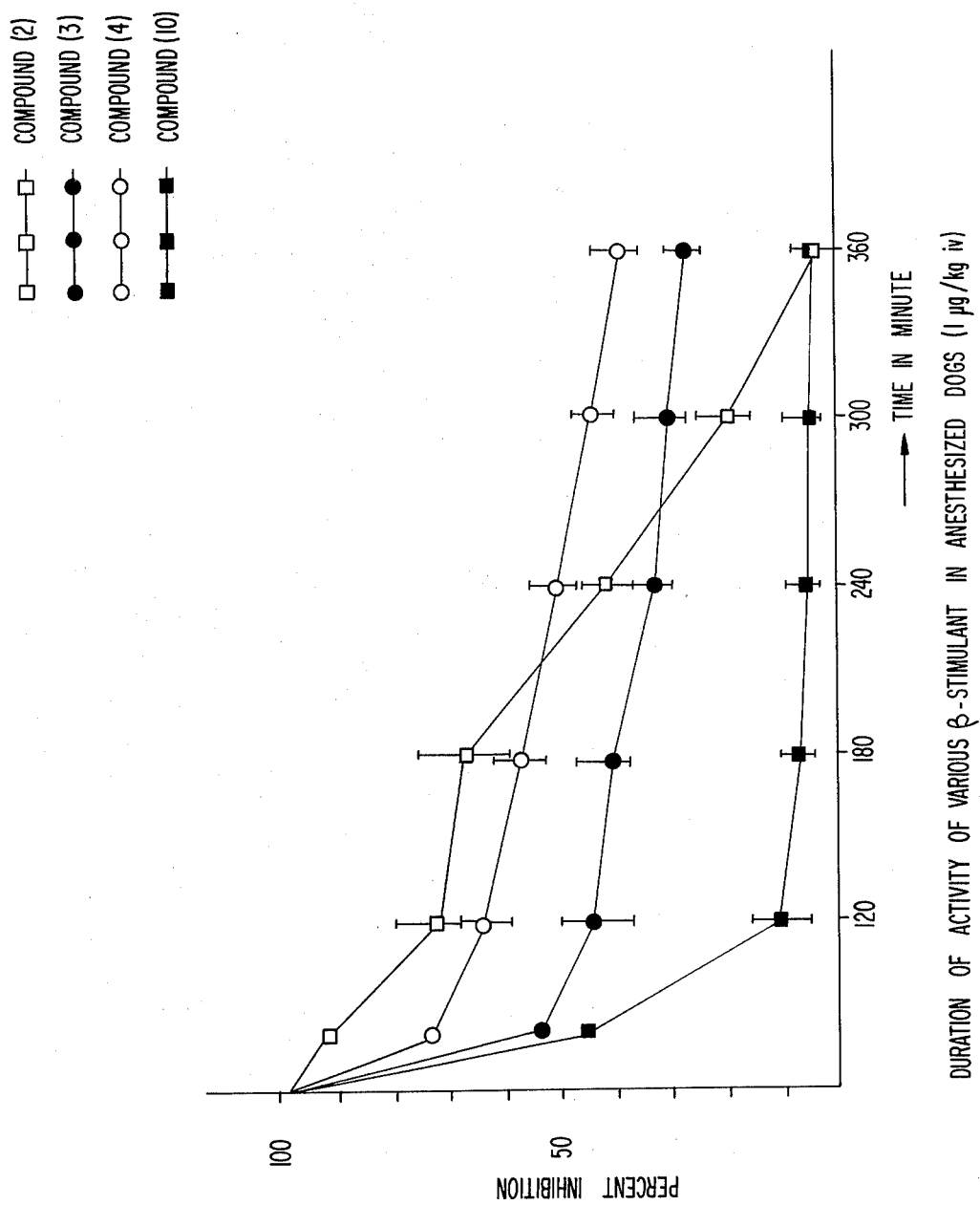

CARBOSTYRIL DERIVATIVES AND PROCESS FOR PREPARING THE SAME

This is a continuation of Ser. No. 756,651, filed Jan. 4, 1977, now abandoned.

BACKGROUND OF THE INVENTION

1. Field of the Invention

This invention relates to carbostyril derivatives and a process for preparing the same. More particularly, this invention relates to carbostyril derivatives represented by the formula (I) hereinafter described, the pharmaceutically acceptable acid addition salts thereof, and a process for preparing the same.

2. Description of the Prior Art

It is well known that certain carbostyril derivatives exhibit useful pharmaceutical activities. Representative compounds of this type have been disclosed in *Journal of Medical Chemistry*, Vol. 15, No. 3, pp. 260–266 (1972), Japanese Patent Publication No. 38789/1971 and *Chemical Abstracts*, 62, 16212e (1965), etc. However, these prior art references do not teach that the compounds having a [1-acyloxy-2-(unsubstituted or-substituted-amine)]alkyl group at the 5-position and/or an acyloxy group at the 8- and/or 2-position of the carbostyril or 3,4-dihydrocarbostyril moiety possess an excellent β-adrenoreceptor stimulating activity.

The carbostyril and 3,4-dihydrocarbostyril derivatives having a 1-hydroxy-2-(substituted-amino)alkyl group at the 5-position and having a substituent at the 1- and/or 8-position of the carbostyril or 3,4-dihydrocarbostyril moiety and the pharmaceutically acceptable acid addition salts thereof are disclosed in Dutch Patent Application No. 74 16844 and U.S. Pat. Nos. 536,515, filed Dec. 26, 1974, 536,516, filed Dec. 26, 1974, 536,703, filed Dec. 26, 1974, 536,704, filed Dec. 26, 1974 and 536,705, filed Dec. 26, 1974, as having a β-adrenoreceptor stimulating activity and being useful as a therapeutic agent such as a bronchodilator, a peripheral vasodilator, an antihypertensive agent and the like, particularly for treating bronchial asthma.

It has now been found that the carbostyril and 3,4-dihydrocarbostyril derivatives having the formulae (I) also exhibit an excellent β-adrenoreceptor stimulating activity.

SUMMARY OF THE INVENTION

An object of the present invention is to provide carbostyril derivative represented by the formula (I):

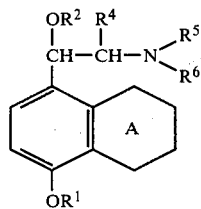

wherein $R^1$ and $R^2$, which may be the same or different, each represents a hydrogen atom, a cycloalkylcarbonyl group, a cycloalkylalkanoyl group, a benzoyl group, an alkanoyl group or a phenylalkylcarbonyl group; $R^4$ represents a hydrogen atom or an alkyl group, $R^5$ and $R^6$, which may be the same or different, each represents a hydrogen atom, an alkyl group, a cycloalkyl group, or a phenylalkyl group, or $R^5$ and $R^6$ may, when taken together with the nitrogen atom to which they are attached, form a 5- or 6-membered substituted or unsubstituted heterocyclic ring containing 1 or 2 nitrogen or oxygen atoms as hetero atoms; and the ring A has a partial structure:

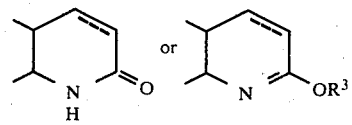

wherein $R^3$ represents a hydrogen atom, a cycloalkylcarbonyl group, a cycloalkylalkanoyl group, a benzoyl group, an alkanoyl group or a phenylalkylcarbonyl group, with the proviso that at least one of $R^1$, $R^2$ and $R^3$ represents a cycloalkylcarbonyl group, a cycloalkylalkanoyl group, a benzoyl group, an alkanoyl group or a phenylalkylcarbonyl group; and the pharmaceutically acceptable acid addition salts thereof.

Another object of this invention is to provide processes for preparing the above carbostyril compounds represented by the formula (I).

BRIEF DESCRIPTION OF THE ACCOMPANYING DRAWING

The FIGURE is a graph showing the relationship between the duration of activity (β-stimulation) and the percent inhibition of histamine-induced bronchospasm after intravenous administration of a comparative compound [Compound (2)] and the compounds of this invention [Compounds (3), (4) and (10)] to anesthesized dogs at a dosage level of 1 μg/kg of doby weight.

DETAILED DESCRIPTION OF THE INVENTION

The term "alkyl" as used herein for $R^4$, $R^5$, and $R^6$ means a straight or branched chain alkyl group having 1 to 4 carbon atoms and includes, for example, a methyl, ethyl, propyl, isopropyl, butyl, sec-butyl, tert-butyl group and the like.

The term "cycloalkylcarbonyl" as used herein means a cycloalkylcarbonyl group having 4 to 8 carbon atoms, for example, a cyclopropylcarbonyl, cyclobutylcarbonyl, cyclopentylcarbonyl, cyclohexylcarbonyl, cycloheptylcarbonyl group and the like.

The term "cycloalkylalkanoyl" as used herein means a cycloalkylalkanoyl group having 3 to 7 carbon atoms in the cycloalkyl moiety and 2 to 4 carbon atoms in the alkanoyl group, for example, a cyclopropylacetyl, 4-cyclopentylbutanoyl, 3-cyclohexylpropanoyl, 3-cycloheptylbutanoyl, 3-cyclohexyl-2-methylpropanoyl group and the like.

The term "benzoyl" as used herein means a benzoyl group which may be substituted with one to three substituents selected from the group consisting of a halogen atoms, a hydroxyl group, a straight or branched chain alkyl group having 1 to 4 carbon atoms, an alkylenedioxy group having 1 to 4 carbon atoms such as a methylenedioxy group, an ethylenedioxy group and the like, an alkoxy group having 1 to 4 carbon atoms such as a methoxy group, an ethoxy group, an isopropoxy group and the like. Typical examples of benzoyl groups are a benzoyl, o-methylbenzoyl, m-ethylbenzoyl, p-isopropylbenzoyl, p-chlorobenzoyl, p-fluorobenzoyl, o-bromobenzoyl, 3,4-ethylenedioxybenzoyl, p-methoxybenzoyl, o-hydroxybenzoyl, p-isopropoxybenzoyl, 3,4- diethoxybenzoyl, 3,4,5-trimethoxybenzoyl group and the like.

The term "cycloalkyl" as used herein means a cycloalkyl group having 4 to 6 carbon atoms, for example, a cyclobutyl, cyclopentyl, cyclohexyl group and the like.

The term "phenylalkyl" as used for $R^5$ and $R^6$ means a phenylalkyl group which may be substituted with 1 to 3 substituents such as those previously described for the benzoyl group, containing 1 to 4 carbon atoms in the alkyl moiety which may be straight or branched chain. Typical examples of phenylalkyl groups are a benzyl, 2-phenylethyl, 3-phenylpropyl, 4-phenylbutyl, 1,1-dimethyl-2-phenylethyl, 2-methyl-3-phenylpropyl, 1-methyl-2-phenylethyl, 3,4-dimethoxyphenetyl, 3,4,5-trimethoxyphenethyl, 3,4-ethylenedioxyphenetyl group and the like.

The term "phenylalkylcarbonyl" as used herein means phenylalkylcarbonyl groups having the same phenylalkyl moiety as the phenylalkyl group previously described for $R^5$, for example, a phenylacetyl, 2-phenylethylcarbonyl, p-methylphenylacetyl, 4-phenylbutylcarbonyl, 2-phenyl-1-methylethylcarbonyl, 3,4-dimethoxyphenetylcarbonyl, 3-(4-chlorophenyl)butylcarbonyl group and the like.

The term "alkanoyl" as used herein means a straight or branched chain alkanoyl group having 2 to 6 carbon atoms, for example, an acetyl, propionyl, butyryl, 2-methylbutyryl, pentanoyl, 2,2-dimethylpropionyl, 3-methylbutanoyl, hexanoyl, 3,3-dimethylbutyryl group and the like.

The term "5- or 6-membered substituted or unsubstituted heterocyclic ring" as used herein means heterocyclic groups containing 1 or 2 nitrogen or oxygen atoms as hetero atoms such as a pyrrolidino, piperidino, morpholino, piperazino or a like group which can be unsubstituted or substituted with an alkyl group having 1 to 4 carbon atoms, such as a methyl, ethyl, isopropyl, tert-butyl group and the like, for example, a 2-methylpiperidino, 3-methylpiperidino, N-methylpiperazino group and the like.

The term "halogen" as used herein includes fluorine, chlorine, bromine and iodine, preferably, chlorine and bromine.

The term "pharmaceutically acceptable acid addition salts" as used herein means those formed with non-toxic inorganic and organic acids which are well known in the art such as, for example, hydrochloric acid, hydrobromic acid, hydroiodic acid, sulfuric acid, phosphoric acid, acetic acid, lactic acid, oxalic acid, malonic acid, succinic acid, maleic acid, fumaric acid, malic acid, mandelic acid, methanesulfonic acid, benzoic acid and the like.

The chemical structure representing carbostyril compounds of the present invention used throughout the sepcification and claims of this invention, i.e., the partial structure having the formula:

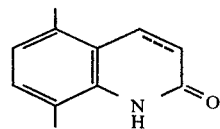

includes both a carbostyril compound and a 3,4-dihydrocarbostyril compound of the partial structure:

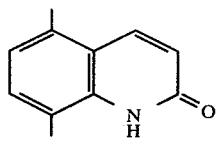

respectively. Such definition is also applied to the compounds having the formula (Id) below.

The corbostyril compounds and the 3,4-dihydrocarbostyril compounds may be present as keto and enol forms with respect to the 2-position, and can be acylated at the 2-position as illustrated below.

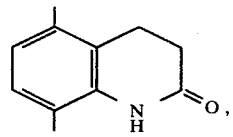

The carbostyril compounds represented by the formula (I) includes the compounds represented by the formulae (Ia), (Ib), (Ic) and (Id).

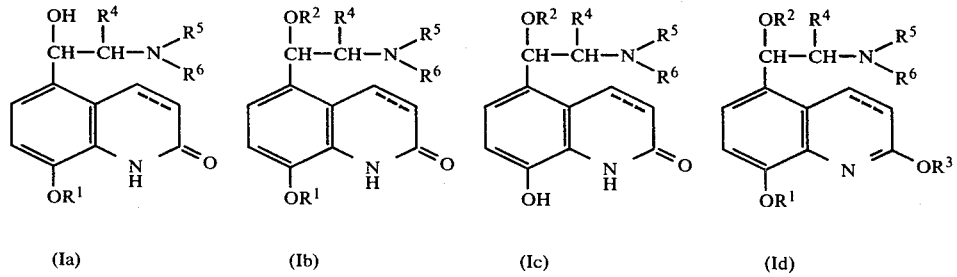

(Ia)　　(Ib)　　(Ic)　　(Id)

wherein $R^1$, $R^2$, $R^4$, $R^5$ and $R^6$ are as defined above.

The carbostyril compounds of the present invention can be prepared from the compounds of the formula (IV) or (V) by acylation according to the processes shown in the Reaction Scheme below.

Reaction Scheme

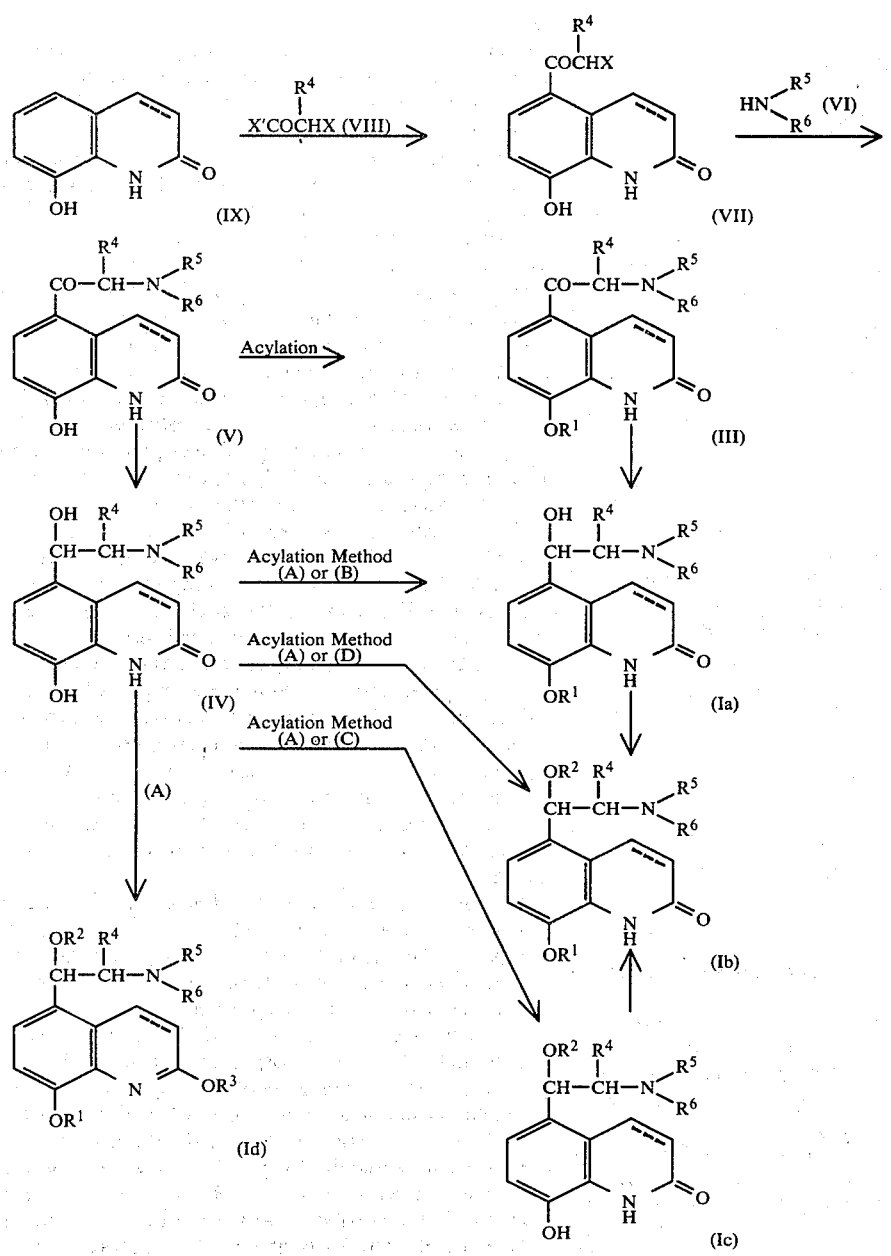

According to the process shown in the Reaction Scheme above, the starting materials of the present invention represented by the formula (IV) can be prepared by:

(1) reacting 8-hydroxycarbostyril or 8-hydroxy-3,4-dihydrocarbostyril of the formula (IX):

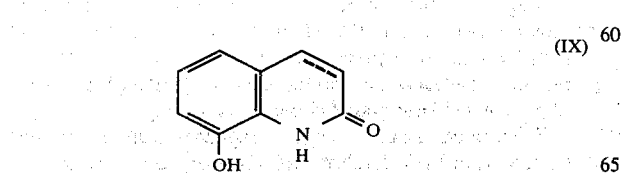

with an α-haloalkanoic acid halide of the formula (VIII):

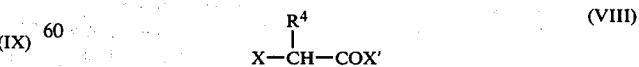

wherein $R^4$ represents a hydrogen atom or an alkyl group having 1 to 4 carbon atoms; and X and X', which may be the same or different, each represents a halogen atom, to obtain a 5-(α-haloalkanoyl)-8-hydroxycarbostyril or 5-(α-haloalkanoyl)-8-hydroxy-3,4-dihydrocarbostyril of the formula (VII):

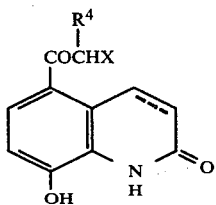

(VII)

wherein R⁴ is as defined above;

(2) reacting the resulting 5-(α-haloalkanoyl)-8-hydroxycarbostyril or 5-(α-haloalkanoyl)-8-hydroxy-3,4-dihydrocarbostyril of the formula (VII) with an amine of the formula (VI):

(VI)

wherein $R^5$ and $R^6$ each represents a hydrogen atom, an alkyl group, a cycloalkyl group or a phenylalkyl group, or $R^5$ and $R^6$ may, when taken together with the nitrogen atom to which they are attached, form a 5- or 6-membered heterocyclic ring, to obtain a 5-(α-substituted-aminoalkanoyl)-8-hydroxycarbostyril or 5-(α-substituted-aminoalkanoyl)-8-hydroxy-3,4-dihydrocarbostyril of the formula (V):

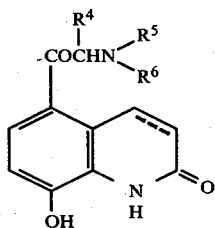

(V)

wherein $R^4$, $R^5$ and $R^6$ are as defined above; and, optionally (3) reducing the resulting 5-(α-substituted-aminoalkanoyl)-8-hydroxycarbostyril or 5-(α-substituted-aminoalkanoyl)-8-hydroxy-3,4-dihydrocarbostyril of the formula (V) with hydrogen by a catalytic reduction or a reduction using a reducing agent.

The α-haloalkanoic acid halide of the formula (VIII) which can be used in this invention includes α-chloropropionyl chloride, α-bromopropionyl chloride, α-chlorobutyryl chloride, α-bromobutyryl chloride, α-bromobutyryl bromide, α-chlorovaleryl chloride and the like.

The reaction between the carbostyril compound of the formula (IX) and the α-haloalkanoic acid halide of the formula (VIII) can be conducted using a Lewis acid as a catalyst, for example, aluminum chloride, aluminum bromide, zinc chloride, ferric chloride, stannic chloride, boron trifluoride, in an amount of about 2 to about 10 moles, preferably 3 to 6 moles, per mole of the starting carbostyril of the formula (IX). The α-haloalkanoic acid halide of the formula (VIII) can be used in an equimolar amount to a large excess relative to the carbostyril of the formula (IX) but generally is used in an amount of from about 2 to about 20 moles, most preferably 2 to 10 moles, per mole of the starting carbostyril of the formula (IX). The reaction can be carried out in the absence of a solvent or in the presence of an appropriate solvent such as carbon disulfide, nitrobenzene, diethyl ether, dioxane and the like and in the presence of the above enumerated catalyst, advantageously under anhydrous conditions, at room temperature (about 0° to 30° C.) to about 150° C., preferably from room temperature to about 80° C. for a period of about 1 to about 20 hours, preferably 4 to 10 hours. The above solvent is usually used in a volume of about 0.5 to 20, preferably 2 to 10, times the volume of the reactants.

The amines of the formula (VI) which can be used in the reaction with the 5-(α-haloalkanoyl)-8-hydroxycarbostyril or 5-(α-haloalkanoyl)-8-hydroxy-3,4-dihydrocarbostyril of the formula (VII) include ammonia, alkylamines, for example, methylamine, ethylamine, n-propylamine, isopropylamine, n-butylamine, sec-butylamine, tert-butylamine, cyclopentylamine, cyclohexylamine; phenylalkylamines, for example, benzylamine, α-methylbenzylamine, α,α-dimethylbenzylamine, phenethylamine, α,α-dimethylphenethylamine and the like; and substituted or unsubstituted heterocyclic amines, for example, pyrrolidine, piperidine, morpholine, piperazine, 2-methylpiperidine, 3-methylpiperidine, N-methylpiperazine and the like.

This reaction between the amine of the formula (VI) and the 5-(α-haloalkanoyl)-8-hydroxycarbostyril or 5-(α-haloalkanoyl)-8-hydroxy-3,4-dihydrocarbostyril of the formula (VII) can be effected in the absence of a solvent since the amine reactant itself also serves as a solvent, but it is advantageous to conduct the reaction in an appropriate solvent. Suitable examples of solvents which can be used include lower alcohols such as methanol, ethanol, isopropanol and the like, ethers such as dioxane, diethyl ether and the like, esters such as ethyl acetate, aromatic hydrocarbons such as benzene, toluene, xylene and the like, nitrile solvents such as acetonitrile and the like. Ethanol and isopropanol are preferred.

This reaction can be effected using an equimolar amount to, especially in the absence of a solvent, a large excess of the amine of the formula (VI), preferably from about 2 to about 10 moles of the amine per mole of the 5-(α-haloalkanoyl)-8-hydroxycarbostyril or 5-(α-haloalkanoyl)-8-hydroxy-3,4-dihydrocarbostyril of the formula (VII) at about atmospheric pressure to about 10 atmospheres at a temperature of from room temperature to the refluxing temperature of the reaction system, preferably at a temperature of 40° to 100° C., in an appropriate solvent or using the amine of the formula (VI) per se as a solvent to obtain a 5-(α-substituted-aminoalkanoyl)-8-hydroxycarbostyril or 5-(α-substituted-aminoalkanoyl)-8-hydroxy-3,4-dihydrocarbostyril of the formula (V).

The reduction of the 5-(α-substituted-aminoalkanoyl)-8-hydroxycarbostyril or 5-(α-substituted-aminoalkanoyl)-8-hydroxy-3,4-dihydrocarbostyril of the formula (V) to the starting compounds of the present invention represented by the formula (IV) can be conducted by a conventional reduction using a reducing agent such as lithium aluminum hydride, sodium borohydride and the like, or a conventional catalytic reduction in the presence of a catalyst such as palladium black, palladium-carbon, Raney nickel, platinum black, platinum oxide and the like and hydrogen.

The above reducing agent can be used in an amount of from about 2 to about 10 moles, preferably 2 to 5 moles, per mole of the carbostyril compound of the formula (V) in a solvent while cooling under atmospheric pressure at a temperature of from about 0° to about 100° C., preferably 20° to 50° C. When sodium borohydride is used as a reducing agent, the solvent is preferably water or an alcohol such as methanol, ethanol and the like, and when lithium aluminum hydride is used as a reducing agent, the solvent is preferably a non-aqueous solvent such as anhydrous diethyl ether, ethyl acetate, tetrahydrofuran and the like.

The catalytic reduction can be carried out using the above catalyst in an amount of from about 0.05 to about 1 mole, preferably 0.1 to 0.5 mole, per mole of the carbostyril compound of the formula (V) in a solvent, for example, water or an alcohol such as methanol, ethanol or isopropanol under a hydrogen atmosphere at a pressure of from about atmospheric pressure to about 100 atmospheres, preferably atmospheric pressure to 50 atmospheres, at a temperature of from room temperature to about 150° C., preferably room temperature to 120° C., advantageously with agitating the reduction system. It is advantageous to carry out the above catalytic reduction at a temperature higher than about 50° C. at atmospheric pressure or at a temperature higher than room temperature under atmospheric pressure.

The 8-hydroxycarbostyril or 8-hydroxy-3,4-dihydrocarbostyril compounds of the formula (IV) obtained above can then be acylated using a carboxylic acid halide or a carboxylic acid anhydride as an acylating agent to produce the compounds of the formulae (Ia), (Ib), (Ic) and (Id). Alternatively, the compound of the formula (Ia) can be produced by acylating the compound of the formula (V) with a carboxylic acid halide or a carboxylic acid anhydride as an acylating agent to produce the compound of the formula (III) and reducing the resulting compound of the formula (III) in the same manner as described for the reduction of the compound of the formula (V) to the compound of the formula (IV).

The acylation of 8-hydroxycarbostyril or 8-hydroxy-3,4-dihydrocarbostyril of the formulae (V) and (IV) obtained above can be conducted using various procedures well known in the art for acylation of the hydroxyl group. Typical procedures which have been found particularly useful in preparing the carbostyril derivatives of this invention are described hereinafter in detail.

The carbostyril compounds of the formula (IV) contain 3 hydroxyl groups including an enol group at the 2-position, and a competitive acylation between these hydroxyl groups is involved in these compounds, i.e., 8-hydroxyl group>2-hydroxyl group or a hydroxyl group in the side chain at the 5-position of the carbostyril nucleus; 8-hydroxyl group>a hydroxyl group in the side chain at the 5-position of the 3,4-dihydrocarbostyril nucleus. Further, O-acylated carbostyril compounds having the formulae (Ia), (Ib), (Ic) and (Id) tend to be reactive to acid or alkali hydrolysis or catalytic reduction, i.e., 2-O-acyl>8-O-acyl or 5-O-acyl, to regenerate hydroxyl groups by cleaving acyl groups. Thus, a wide variety of acylated carbostyril derivatives can be produced by appropriately selecting the acylation conditions as well as hydrolysis and/or reduction conditions.

The acylation procedures used in the present invention can be classified as Acylation Method (A) to Acylation Method (D) according to the acylation positions, as hereinafter described in greater detail.

It is to be noted that the terms "carboxylic acid halide" and "carboxylic acid anhydride" used herein for acylating agents are those containing an acyl moiety corresponding to the acyl group $R^1$, $R^2$ or $R^3$ as described above.

Under the acylation conditions employed in Acylation Method (A), at least one hydroxyl group attached to the 2-position, attached to the side chain at the 5-position and attached to the 8-position of the carbostyril or 3,4-dihydrocarbostyril derivatives can be acylated thereby producing a 2-acylated compound, an 8-acylated compound or a compound having an acyl group in the side chain attached to the 5-position of the carbostyril or 3,4-dihydrocarbostyril compound, as a single compound or a mixture thereof. The resulting acylated product can be isolated by conventional procedures, for example, solvent extraction, fractional recrystallization, column chromatography, thin-layer chromatography or a combination of these isolation procedures to obtain a single acylated product of the present invention.

Under acylation conditions employed in Acylation Methods (B) to (C), an 8-hydroxyl group, a 5-hydroxyl group or both 5- and 8-hydroxyl groups of the carbostyril or 3,4-dihydrocarbostyril compounds can be selectively acylated by taking advantage of the difference in reactivity between these hydroxyl groups with an acylating agent.

ACYLATION METHOD (A)

This acylation method can be advantageously conducted in a conventional manner using a carboxylic acid halide or carboxylic acid anhydride as an acylating agent in the absence of a solvent or in the presence of an inert solvent, for example, ethers such as dioxane, tetrahydrofuran and the like, halogenated hydrocarbons such as methylene chloride, 1,2-dichloroethane and the like, carboxylic acids such as acetic acid, propionic acid, trichloroacetic acid, trifluoroacetic acid and the like, pyridine, dimethyl sulfoxide, dimethylformamide, hexamethylphosphoric acid triamide and the like.

The amount of acylating agents used in this acylation method is not critical, but is preferably about 0.5 mole to a molar excess per mole of the carbostyril compound to be acylated.

The acylation can be advantageously carried out at a temperature of from about −30° C. to about 200° C., preferably room temperature of 70° C., for a period of from about 1 hour to about 24 hours. As is apparent to one skilled in the art, the higher the acylation temperature is the shorter is the acylation time.

Alternatively, an inorganic basic compound or an organic tertiary amine can be used in the acylation reaction as a hydrogen halide acceptor. Typical examples of such hydrogen halide acceptors are sodium hydroxide, potassium hydroxide, sodium bicarbonate, sodium carbonate, triethylamine, trimethylamine, pyridine, quinoline and the like.

ACYLATION METHOD (B)

This acylation method can be used for acylation of the hydroxyl group at the 8-position of the carbostyril or 3,4-dihydrocarbostyril compounds.

The acylation can be conducted by first reacting a carbostyril compound having a hydroxyl group at the 8-position with an alkali metal compound in an inert solvent to convert the hydroxyl group to an alkali metal salt thereof in a usual manner. Suitable inert solvents which can be used in this acylation include alcohols such as methanol, ethanol and the like, ethers such as dioxane, tetrahydrofuran and the like, and halogenated hydrocarbons such as methylene chloride, 1,2-dichloroethane and the like. Examples of alkali metal compounds which can be used in this acylation method include alkali metal alkoxides such as sodium methoxide, sodium ethoxide, potassium ethoxide and the like, alkali metals such as sodium metal, potassium metal and the like, and alkali metal hydroxides such as sodium hydroxide, potassium hydroxide and the like.

After completion of the conversion, the solvent is removed by evaporation, and the resulting alkali metal salt is then reacted with a carboxylic acid halide as an acylating agent in a solvent at a temperature of about 0° C. to about 70° C., preferably at 0° C. to room temperature, for a period of about 1 to 12 hours to obtain an 8-acylated carbostyril compound. Suitable solvents which can be used for this purpose include ethers such as dioxane, tetrahydrofuran and the like, halogenated hydrocarbons such as methylene chloride, 1,2-dichloroethane and the like, pyridine, dimethyl sulfoxide, dimethylformamide, hexamethylphosphoric acid triamide and the like.

Thus, the hydroxyl group at the 8-position can be selectively acylated by first converting the hydroxyl group into an alkali metal salt thereof and then acylating the resulting alkali metal salt.

Alternatively, the above acylation method can be conducted without removal of the solvent used for the conversion of the 8-hydroxyl group into an alkali metal salt thereof, if the solvent is inert to the acylating agent used in the subsequent acylation step. Suitable examples of such solvents are those solvents other than alcohols described above.

In this acylation method, the alkali metal compound and the acylating agent can be used in an amount of about 0.5 to about 2 moles, preferably an equimolar amount of 1.3 moles, per mole of the carbostyril or 3,4-dihydrocarbostyril compound to by acylated.

Further, the acylation can be carried out without converting an 8-hydroxyl group into an alkali metal salt thereof if pyridine is used as a solvent for acylation. In such a procedure, the acylation can be conducted using a carboxylic acid halide or a carboxylic acid anhydride as an acylating agent in an approximately equimolar amount to about 1.5 moles per mole of the carbostyril or 3,4-dihydrocarbostyril compound to be acylated at a temperature of about 0° C. to 70° C., preferably at 0° C. to room temperature, for a period of about 30 minutes to about 12 hours.

ACYLATION METHOD (C)

This acylation method can be used for acylation of the hydroxyl group in the side chain attached to the 5-position of the carbostyril or 3,4-dihydrocarbostyril compounds.

The acylation can be conducted by first protecting the 8-hydroxyl group with an appropriate protective group, and then acylating the 5-hydroxyl group with an acylating agent, followed by removing the protective group by catalytic reduction.

Suitable examples of protective groups which can be used are a benzyl group, a p-nitrobenzyl group and the like.

The acylation can be advantageously carried out using a conventional procedure employing a carboxylic acid halide or a carboxylic acid anhydride as an acylating agent in an amount of about 0.5 mole to a molar excess, preferably an equimolar amount to 1.3 moles, of the acylating agent per mole of the carbostyril or 3,4-dihydrocarbostyril compound to be acylated, at a temperature of about −30° C. to about 200° C., preferably room temperature to 70° C., for a period of from about 1 hour to about 24 hours in the presence or absence of a solvent.

Suitable solvents which can be used in this acylation method are those described above for Acylation Method (A).

The inorganic basic compound or the organic tertiary amines as described for Acylation Method (A) can also be used in this acylation method as a hydrogen halide acceptor.

The catalytic reduction for the removal of the protective group at the 8-position can be conducted by a conventional procedure well known in the art for removal of a benzyl group from an —O—benzyl group, and advantageously carried out by catalytically reducing the 8-protected carbostyril or 3,4-dihydrocarbostyril compound in the presence of a catalyst such as palladium, palladium-carbon, palladium black, Raney nickel and the like, at a temperature of from room temperature to about 50° C. at a pressure ranging from atmospheric pressure to about 3 atms. for a period of about 1 to 12 hours in the presence of a solvent such as methanol, ethanol, benzene, toluene, diethyl ether, dioxane and the like. However, it is to be noted that these processing parameters and type of solvents are not critical and can widely be varied depending upon the type of acylating agent used.

ACYLATION METHOD (D)

This acylation method can be used for acylation of both the hydroxyl group at 8-position and the hydroxyl group in the side chain attached to the 5-position of the carbostyril or 3,4-dihydrocarbostyril compound.

The acylation can be conducted using a carboxylic acid halide or a carboxylic acid anhydride as an acylating agent in the absence of a solvent or in the presence of an inert aprotic solvent, for example, ethers such as dioxane, tetrahydrofuran and the like, halogenated hydrocarbons such as methylene chloride, 1,2-dichloroethane and the like; a strongly acidic to weakly acidic solvent, for example, carboxylic acids such as acetic acid, propionic acid, trichloroacetic acid, trifluoroacetic acid and the like; or pyridine, dimethyl sulfoxide, dimethylformamide, hexamethylphosphoric acid amide and the like, at a temperature of approximately room temperature to about 150° C., preferably 50° to 90° C., for a period of about 1 to about 6 hours. Particularly preferred solvents are strongly acidic to weakly acidic solvents such as trifluoroacetic acid, trichloroacetic acid, propionic acid, acetic acid and the like, or a mixture of the aprotic solvent described above and the strongly acidic to weakly acidic solvent. An inorganic basic compound or an organic tertiary amine as set forth above the Acylation Method (A) can also be used in this acylation reaction when an aprotic solvent is used for the acylation. In this acylation method, the acylating agent can be used in an amount of about 1.5 moles to a molar excess, preferably 2.0 moles to 2.5 moles, per mole of the carbostyril or 3,4-dihydrocarbostyril compound to be acylated.

Further, carbostyril or 3,4-dihydrocarbostyril compounds in which $R^1$, $R^2$ and $R^3$ represent different acyl group, for example, compounds of the formula (Id) in which $R_1$ and $R_2$ represent different acyl groups and compounds of the formula (Id) in which $R^1$, $R^2$ and $R^3$ represent different acyl groups, can be obtained using various combinations of Acylation Methods (A) to (D). As is apparent to one skilled in the art, these compounds can also be derived from compounds of the formulae (Ia), (Ib), (Ic), (Id) and (III) by using various combinations of acylation, hydrolysis and/or reduction procedures as previously described.

Thus, the carbostyril derivatives of the present invention represented by the formula (I) can be prepared by the following alternative procedures:

(1) A carbostyril derivative represented by the formula (I):

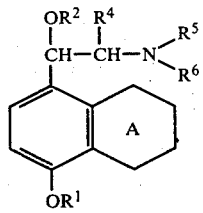

wherein $R^1$, $R^2$, $R^4$, $R^5$ and $R^6$ are as defined above, and the ring A has a partial structure:

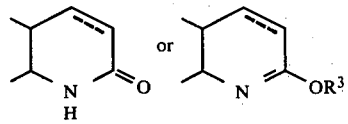

wherein $R^3$ is as defined above, with the proviso that at least one of $R^1$, $R^2$ and $R^3$ represents a cycloalkylcarbonyl group, a cycloalkylalkanoyl group, a benzoyl group, an alkanoyl group or a phenylalkylcarbonyl group, and pharmaceutically acceptable acid addition salts of the carbostyril derivative of the formula (I) can be prepared by acylating a carbostyril derivative represented by the formula (X):

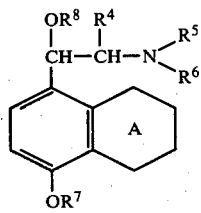

wherein $R^4$, $R^5$ and $R^6$ are as defined above, and the ring A has a partial structure:

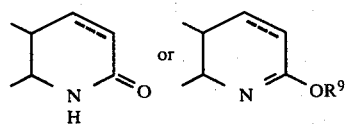

and $R^7$, $R^8$ and $R^9$, which may be the same or different, each represents a hydrogen atom, a cycloalkylcarbonyl group, a cycloalkylalkanoyl group, a benzoyl group, an alkanoyl group or a phenylalkylcarbonyl group, with the proviso that at least one of $R^7$, $R^8$ and $R^9$ represents a hydrogen atom, with a carboxylic acid halide or a carboxylic acid anhydride at a temperature of about $-30°$ C. to about $200°$ C. for about 1 hour to about 24 hours. Thus, compounds of the formulae (Ia) and (Ib) can be prepared from the compounds of the formulae (IV) and (Ic), respectively.

(2) A carbostyril derivative represented by the formula (Ia) or (Ib):

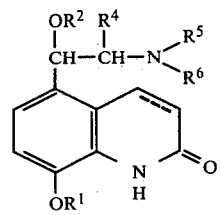

wherein $R^2$, $R^4$, $R^5$ and $R^6$ are as defined above, $R^1$ represents a cycloalkylcarbonyl group, a cycloalkylalkanoyl group, a benzoyl group, an alkanoyl group or a phenylalkylcarbonyl group, and pharmaceutically acceptable acid addition salts of the carbostyril derivative of the formula (Ia) or (Ib) can be prepared by reacting a carbostyril or 3,4-dihydrocarbostyril compound of the formula (Ic) or (IV):

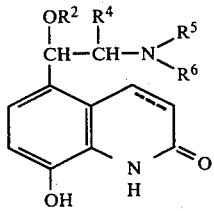

wherein $R^2$, $R^4$, $R^5$ and $R^6$ are as defined above, with an alkali metal compound to convert the 8-hydroxyl group of said carbostyril or 3,4-dihydrocarbostyril compound of the formula (Ic) or (IV) into an alkali metal salt thereof, and acylating the resulting carbostyril or 3,4-dihydrocarbostyril compound with a carboxylic acid halide or a carboxylic acid anhydride at a temperature of about $0°$ C. to about $70°$ C. for about 1 to 12 hours, according to the process (1) above.

(3) A carbostyril derivative represented by the formula (Ia) or (Ib):

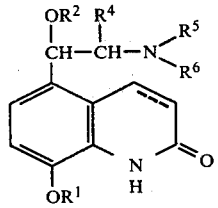

wherein $R^2$, $R^4$, $R^5$ and $R^6$ are as defined above, $R^1$ represents a cycloalkylcarbonyl group, a cycloalkylalkanoyl group, a benzoyl group, an alkanoyl group or a phenylalkylcarbonyl group, and pharmaceutically acceptable acid addition salts of the carbostyril derivatives of the formula (Ia) or (Ib) can be prepared by acylating a carbostyril or 3,4-dihydrocarbostyril compound represented by the formula (Ic) or (IV):

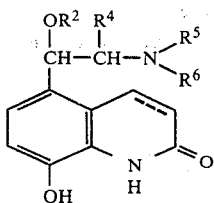

wherein $R^2$, $R^4$, $R^5$ and $R^6$ are as defined above, with a carboxylic acid halide or a carboxylic acid anhydride in an amount of an approximately equimolar amount to about 1.5 moles per mole of said carbostyril or 3,4-dihydrocarbostyril compound of the formula (Ic) or (IV) in the presence of pyridine at a temperature of about 0° C. to about 70° C. for about 30 minutes to about 12 hours, according to the process (1) above.

(4) A carbostyril derivative represented by the formula (Ib) or (Ic):

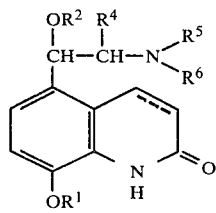

wherein $R^1$, $R^4$, $R^5$ and $R^6$ are as defined above, $R^2$ represents a cycloalkylcarbonyl group, a cycloalkylalkanoyl group, a benzoyl group, an alkanoyl group or a phenylalkylcarbonyl group, and pharmaceutically acceptable acid addition salts of the carbostyril derivative of the formula (Ib) or (Ic) can be prepared by protecting an 8-hydroxyl group of a carbostyril or 3,4-dihydrocarbostyril compound of the formula (Ia) or (IV)

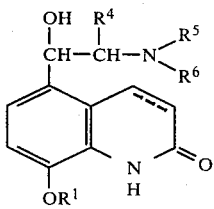

wherein $R^1$, $R^4$, $R^5$ and $R^6$ are as defined above, with a protective group, subjecting the resulting 8-protected 8-acyl carbostyril and 3,4-dihydrocarbostyril compound to acylation with a carboxylic acid halide or a carboxylic acid anhydride in an amount of at least about 0.5 mole per mole of said 8-protected 8-acyl carbostyril and 3,4-dihydrocarbostyril compound at a temperature of about −30° C. to about 200° C. for about 1 hour to about 24 hours, and catalytically reducing the resulting compound at a temperature of room temperature to about 50° C. under a pressure of atmospheric pressure to about 3 atms. for about 1 hour to about 12 hours in the presence of a solvent to remove the 8-protective group, according to the process (1) above.

(5) A carbostyril derivative represented by the formula (Ib):

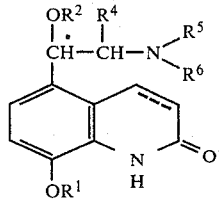

wherein $R^4$, $R^5$ and $R^6$ are as defined above, and both $R^1$ and $R^2$ are the same and represent a cycloalkylcarbonyl group, a cycloalkylalkanoyl group, a benzoyl group, an alkanoyl group or a phenylalkylcarbonyl group, and said addition salts of the carbostyril derivative of the formula (Ib) can be prepared by acylating a carbostyril or 3,4-dihydrocarbostyril compound of the formula (IV):

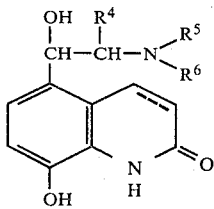

wherein $R^4$, $R^5$ and $R^6$ are as defined abobe, with a carboxylic acid halide or a carboxylic acid anhydride in an amount at least about 1.5 moles per mole of said carbostyril or 3,4-dihydrocarbostyril compound of the formula (IV) at a temperature of approximately room temperature to about 150° C. for about 1 hour to about 6 hours, according to the process (1) above.

Representative compounds of the present invention having the formulae (Ia), (Ib), (Ic) and (Id) are as follows:

8-Cyclohexylcarbonyloxy-5-(1-hydroxy-2-isopropylaminobutyl)carbostyril,

8-Cycloheptylcarbonyloxy-5-(1-hydroxy-2-tert-butylaminoethyl)-3,4-dihdrocarbostyril, 8-Cyclopropylcarbonyloxy-5-(1-hydroxy-2-isopropylaminobutyl)carbostyril, 8-Cyclopentylcarbonyloxy-5-(1-hydroxy-2-isopropylaminobutyl)carbostyril, 8-Cyclobutylacetoxy-5-(1-hydroxy-2-ethylaminobutyl)-carbostyril, 8-(3-Cyclohexylpropanoyloxy)-5-(1-hydroxy-2-isopropylaminopentyl)-3,4-dihydrocarbostyril, 8-(3-Cyclohexyl-2-methylpropanoyloxy)-5-(1-hydroxy-2-isopropylaminobutyl)carbostyril, 8-Cyclohexylacetoxy-5-(1-hydroxy-2-isopropylaminobutyl)-3,4-dihydrocarbostyril, 8-Benzoyloxy-5-(1-hydroxy-2-isorpopylaminobutyl)-carbostyril, 8-(4-Chlorobenzoyloxy)-5-(1-hydroxy-2-tert-butylaminobutyl)carbostyril, 8-(4-Fluorobenzoyloxy)-5-(1-hydroxy-2-isopropylaminobutyl)carbostyril, 8-(2-Bromobenzoyloxy)-5-(1-hydroxy-2-butylaminopropyl)-3,4-dihydrocarbostyril, 8-(3,4-Ethylenedioxybenzoyloxy)-5-(1-hydroxy-2-isopropylaminobutyl)-3,4-dihydrocarbostyril, 8-(3-Methoxybenzoyloxy)-5-(1-hyroxy-2-isopropylaminobutyl)-3,4-dihydrocarbostyril, 8-(4-Isopropoxybenzoyloxy)-5-(1-hydroxy-2-isopropylaminobutyl)carbostyril,
8-(4-Methylbenzoyloxy)-5-(1-hydroxy-2-isopropylaminobutyl)carbostyril,
8-(3-Ethylbenzoyloxy)-5-(1-hydroxy-2-isopropylaminobutyl)-3,4-dihydrocarbostyril,
8-(2-Propylbenzoyloxy)-5-(1-hydroxy-tert-butylaminoethyl)carbostyril,
8-(4-Isopropylbenzoyloxy)-5-(1-hydroxy-2-isopropylaminobutyl)carbostyril,
8-Cyclohexylcarbonyloxy-5-(1-cyclohexylcarbonyloxy-2-isopropylaminobutyl)carbostyril,
8-Cyclobutylcarbonyloxy-5-(1-cycloheptylcarbonyloxy-2-tert-butylaminobutyl)carbostyril,
8-(4-Methylbenzoyloxy)-5-(1-cyclobutylcarbonyloxy-2-isopropylaminoethyl)carbostyril,
8-(3,4-Methylenedioxybenzoyloxy)-5-(1-p-methylbenzoyloxy-2-isopropylaminobutyl)carbostyril,
8-Cyclohexylacetyloxy-5-(1-p-chlorobenzoyloxy-2-isopropylaminobutyl)-3,4-dihydrocarbostyril,
8-Cyclohexylcarbonyloxy-5-(1-benzoyloxy-2-isopropylaminobutyl)-3,4-dihydrocarbostyril,
8-Cyclohexylcarbonyloxy-5-(1-cyclohexylacetoxy-2-isopropylaminobutyl)carbostyril,
8-Cyclohexylcarbonyloxy-5-(1-hydroxy-2-$\alpha,\alpha$-dimethylphenethylaminobutyl)carbostyril,
8-(p-Methylbenzoyloxy)-5-(1-hydroxy-3',4'-dimethoxyphenethylaminobutyl)carbostyril.
8-(p-Chlorobenzoyloxy)-5-(1-hydroxy-2-3'-phenyl-1'-methylpropylaminobutyl)carbostyril,
8-Cyclohexylcarbonyloxy-5-(1-hydroxy-2-phenethylaminobutyl)carbostyril,
8-Cyclohexylacetoxy-5-(1-cyclohexylcarbonyloxy-2-benzylaminobutyl)carbostyril,
8-Cyclohexylcarbonyloxy-5-(1-p-methylbenzoyloxy-2-phenethylaminobutyl)carbostyril,
8-p-Chlorobenzoyloxy-5-(1-p-chlorobenzoyloxy-2-benzylaminobutyl)carbostyril,
8-Cyclopentylcarbonyloxy-5-(1-cyclopentylcarbonyloxy-2-3',4'-dimethoxyphenethylaminobutyl)carbostyril,
8-(3-Cyclohexylpropanoyloxy)-5-(1-hydroxy-2-ethylaminobutyl)carbostyril,
8-(3,4-Methylenedioxybenzoyloxy)-5-(1-3',4'-methylenedioxybenzoyloxy-2-isopropylaminopropyl)carbostyril,
8-(3,4-Dimethoxybenzoyloxy)-5-(1-hydroxy-2-isopropylaminobutyl)carbostyril,
8-Cyclohexylcarbonyloxy-5-(1-benzoyloxy-2-isopropylaminobutyl)carbostyril,
8-Phenylacetoxy-5-(1-hydroxy-2-isopropylaminobutyl)carbostyril,
8-(3,4-Dimethoxyphenethylcarbonyloxy)-5-(1-hydroxy-2-isopropylaminobutyl)carbostyril,
8-(2-Phenyl-1-methylethylcarbonyloxy)-5-(1-hydroxy-2-isopropylaminobutyl)-3,4-dihydrocarbostyril,
8-(p-Methylphenylacetoxy)-5-(1-hydroxy-2-tert-butylaminobutyl)carbostyril,
8-(3-p-Chlorophenylbutylcarbonyloxy)-5-(1-hydroxy-2-tert-butylaminopropyl)-3,4-dihydrocarbostyril,
8-Acetoxy-5-(1-hydroxy-2-isopropylaminobutyl)carbostyril,
8-Butyryloxy-5-(1-butyryloxy-2-tert-butylaminobutyl)carbostyril,
8-Hexanoyloxy-5-(1-hydroxy-2-phenethylaminobutyl)-3,4-dihydrocarbostyril,
8-(2,2-Dimethylpropionyl-5-(1-hydroxy-2-phenethylaminobutyl)carbostyril,
8-Hydroxy-5-(1-hydroxy-2-isopropylaminoethyl)-2-(2-methylbutyryl)quinoline,
8-(3,3-Dimethylbutyryloxy)-5-(1-hydroxy-2-isopropylaminobutyl)carbostyril,
8-Acetoxy-5-(1-propionyloxy-2-isopropylaminobutyl)carbostyril,
8-(2,2-Dimethylpropionyloxy)-5-(1-cyclohexylcarbonyloxy-2-ethylaminobutyl)carbostyril,
8-(3-Methylbutanoyloxy)-5-(1-benzoyloxy-2-tert-butylaminobutyl)-3,4-dihydrocarbostyril,
2,8-Diacetoxy-5-(1-acetoxy-2-isopropylaminobutyl)quinoline,
8-(3,3-Dimethylbutyryloxy)-5-[1-phenylacetyloxy-2-(3,4-dimethoxyphenethylamino)butyl]-2-cyclohexylcarbonyloxyquinoline,
2,8-(4-Methylbenzoyloxy)-5-[1-(4-methylbenzoyloxy)-2-(3,4-methylenedioxyphenethylamino)butyl]quinoline,
8-(2,2-Dimethylpropionyloxy)-5-[1-hydroxy-2-(3,4-methylenedioxyphenethylamino)butyl]carbostyril,
8-Acetoxy-5-(1-hydroxy-2-N,N-diethylaminobutyl)carbostyril,
8-(3,3-Dimethylbutyryloxy)-5-(1-hydroxy-2-N,N-methylethylaminobutyl)-3,4-dihydrocarbostyril,
8-(p-Methylbenzoyloxy)-5-(1-p-methylbenzoyloxy-2-N,N-dipropylaminobutyl)carbostyril,
8-(2,2-Dimethylpropionyloxy)-5-(1-hydroxy-2-morpholinobutyl)carbostyril,
8-(p-Methylbenzoyloxy)-5-(1-hydroxy-2-piperadinobutyl)3,4-dihydrocarbostyril,
8-Cyclohexylcarbonyloxy-5-(1-cyclohexylcarbonyloxy-2-piperidinobutyl)carbostyril,
8-Propionyloxy-5-(1-hydroxy-2-pyrrolidinobutyl)-3,4-dihydrocarbostyril,
8-Acetoxy-5-(1-hydroxy-2-N-methylpiperazinobutyl)carbostyril,
2,8-Diacetoxy-5-(1-acetoxy-2-imidazolidinoethyl)-3,4-dihydrocarbostyril, and
8-(p-Methylbenzoyloxy)-5-[1-hydroxy-2-(2,5-dimethylpiperazino)butyl]carbostyril.

The present invention is further illustrated in greater detail by the following Reference Examples and Examples, but these Examples are given for illustrative purpose only and are not to be construed as limiting the present invention. Unless otherwise indicated, all parts, percents, ratios and the like are by weight.

REFERENCE EXAMPLE 1

(A) 2.7 g of 8-hydroxycarbostyril and 37 ml of chloroacetyl chloride were dissolved in 250 ml of nitrobenzene, and 85 g of aluminum chloride was added slowly to the solution. The resulting mixture was then stirred at a temperature of 70° C. for 20 hours. 500 ml of a 10% hydrochloric acid aqueous solution was added to the mixture and nitrobenzene was removed by steam distillation. After allowing the mixture to cool, the precipitated crystals were separated by filtration, washed with 300 ml of hot water and recrystallized from methanol to obtain 14.0 g of 5-chloroacetyl-8-hydroxycarbostyril as light yellow crystals having a melting point of 285°–287° C. (with decomposition).

12.6 g of 5-chloroacetyl-8-hydroxycarbostyril obtained above was suspended in 130 ml of isopropanol, and 25.5 g of isopropylamine was added dropwise to the suspension while stirring followed by stirring for 3 hours at a temperature of 55 to 60° C. After allowing the mixture to cool, the mixture was adjusted to a pH of 2–3 with concentrated hydrochloric acid. The precipitated crystals were separated by filtration, washed with acetone and recrystallized from a mixture of methanol and dimethylformamide to obtain 6.5 g of 5-isopropylaminoacetyl-8-hydroxycarbostyril hydrochloride represented by the formula (V) as light yellow crystals having a melting point of 286°–288° C. (with decomposition).

(B) 1.0 g of 5-isopropylaminoacetyl-8-hydroxycarbostyril hydrochloride obtained in (A) above was dissolved in 40 ml of water, and, in the presence of 0.5 g of a palladium-carbon catalyst, hydrogen gas was bubbled into the solution while maintaining the solution at a temperature of 35°–40° C. with stirring to reduce the starting material. After completion of the reduction, the catalyst was removed by filtration, and the filtrate was concentrated to dryness under reduced pressure. Addition of ethanol to the residue followed by concentration to dryness was repated to completely remove any remaining water, and acetone was added to the residue to crystallize the product. The crystalline product thus obtained was recrystallized from ethanol-acetone to obtain 0.4 g of 5-(2-isopropylamino-1-hydroxyethyl)-8-hydroxycarbostyril hydrochloride of the formula (IV) having a melting point of 210°–212° C. (with decomposition) as a light yellow amorphous compound.

REFERENCE EXAMPLE 2

50 ml of pyridine was added to 2.5 g of 8-hydroxy-5-(α-isopropylaminobutyryl)carbostyril, and 5 ml of isobutyryl chloride was added dropwise to the mixture while cooling with ice-water and stirring followed by stirring for 2 hours. After addition of about 500 ml of diethyl ether, the precipitate formed was washed with diethyl ether and stirred in a small amount of cold water. The precipitate was separated by filtration, washed successively with a small amount of water, acetone and diethyl ether to obtain a crystalline product which was then recrystallized from acetone to obtain 2.1 g of 8-isobutyryloxy-5-(α-Isopropylaminobutyryl)carbostyril hydrochloride having a melting point of 231°–233° C. (with decomposition).

REFERENCE EXAMPLE 3

20 ml of pyridine was added to 1 g of 8-hydroxy-5-(α-isopropylaminobutyryl)carbostyril, and 2 ml of isobutyryl chloride was added dropwise to the mixture while cooling with ice-water and stirring followed by stirring for 3 hours and for 2 hours at a temperature of 35°–40° C. After addition of about 200 ml of diethyl ether, the precipitate formed was stirred in a small amount of cold water and then washed successively with acetone and diethyl ehter. The resulting crystalline product was then recrystallized from acetone to obtain 0.6 g of 2,8-bis(isobutyryloxy)-5-(α-isopropylaminobutyryl)quinoline hydrochloride having a melting point of 214°–215° C. (with coloration and decomposition).

EXAMPLE 1

12 ml of pyridine was added to 0.4 g of 5-(1-hydroxy-2-isopropylaminobutyl)-8-hydroxycarbostyril, and 0.6 ml of isobutyryl chloride was added dropwise to the mixture while cooling with ice-water and stirring followed by stirring for 3 hours. After addition of about 200 ml of diethyl ether, the precipitate formed was washed thoroughly with diethyl ether and dissolved in 50 ml of water. The solution was washed with dichloroethane and the aqueous layer was concentrated to dryness. Acetone was added to the residue to crystallize the product which was then recrystallized from acetone to obtain 0.33 g of 5-(1-hydroxy-2-isopropylaminobutyl)-8-isobutyryloxycarbostyril hydrochloride having a melting point of 228°–229° C. (with coloration and decomposition).

EXAMPLE 2

25 ml of pyridine was added to 1 g of 5-(1-hydroxy-2-isopropylaminobutyl)-8-hydroxy-3,4-dihydrocarbostyril hydrochloride, and 3 ml of isobutyryl chloride was added dropwise to the mixture while cooling with ice-water and stirring followed by stirring for 3 hours. After addition of about 200 ml of diethyl ether, acetone was added to the precipitate formed to obtain a crystalline product. The product thus obtained was recrystallized from acetone to obtain 0.8 g of 5-(1-hydroxy-2-isopropylaminobutyl)-8-isobutyryloxy-3,4-dihydrocarbostyril hydrochloride having a melting point of 239°–240° C. (with coloration and decomposition).

EXAMPLE 3

1 g of 5-(1-hydroxy-2-isopropylaminobutyl)-8-hydroxycarbostyril hydrochloride was dissolved in 10 ml of isobutyric anhydride, and several drops of concentrated sulfuric acid was added to the solution. After stirring the mixture for 2 hours at a temperature of 60° C., 100 ml of diethyl ether was added to the mixture and the precipitate formed was separated by filtration. The precipitate was then dissolved in 20 ml of water and the solution was adjusted to a pH of 7–7.5 with a saturated aqueous solution of sodium bicarbonate while cooling with ice. The resulting mixture was extracted three times with 20 ml portions of diethyl ether. The combined extracts were dried over anhydrous sodium sulfate and concentrated under reduced pressure while cooling. The residue thus obtained was recrystallized from a mixture of diethyl ether and petroleum ether to obtain 0.75 g of 5-(1-isobutyryloxy-2-isopropylaminobutyl)-8-isobutyryloxycarbostyril having a melting point of 124°–125° C.

EXAMPLE 4

3 ml of isobutyric anhydride was added to 1 g of 5-(1-hydroxy-2-isopropylaminobutyl)-8-hydroxycarbostyril, and the mixture was stirred for 30 minutes at a temperature of 60° C. Petroleum ether was added to the reaction mixture, and the mixture was adjusted to a pH of 1–2 with concentrated hydrochloric acid. The precipitate formed was separated by filtration and, after drying the precipitate, it was recrystallized from a mixture of methanol and diethyl ether to obtain 1.1 g of 5-(1-isobutyryloxy-2-isopropylaminobutyl)-8-isobutyryloxycarbostyril hydrochloride monohydrate having a melting point of 198°–199° C.

EXAMPLE 5

3 ml of isobutyric anhydride was added to 0.7 g of 5-(1-hydroxy-2-ethylaminobutyl)-8-hydroxycarbostyril, and the mixture was stirred for 30 minutes at a temperature of 60° C. Petroleum ether was added to the reaction mixture, and the mixture was adjusted to a pH of 1–2 with concentrated hydrochlric acid. The precipitate formed was separated by filtration and, after drying the precipitate, it was recrystallized from a mixture of methanol and diethyl ether to obtain 0.8 g of 5-(1-isobutyryloxy-2-ethylaminobutyl)-8-isobutyryloxycarbostyril hydrochloride having a melting point of 197°–198° C.

EXAMPLE 6

20 ml of pyridine was added to 1 g of 5-(1-hydroxy-2-isopropylaminobutyl)-8-hydroxycarbostyril, and 3 ml of isobutyryl chloride was added dropwise to the mixture while cooling with ice-water and stirring followed by stirring for an additional 2 hours. The precipitate formed was separated by filtration, and about 500 ml of diethyl ether was added to the filtrate. The precipitate formed was washed thoroughly with diethyl ether, and water was added to the precipitate. The water-insoluble substance was separated by filtration, washed with water and, after drying, recrystallized from a mixture of acetone and diethyl ether to obtain 1.2 g of 2,8-diisobutyryloxy-5-(1-isobutyryloxy-2-isopropylaminobutyl)quinoline hydrochloride having a melting point of 187°–188° C.

EXAMPLES 7–10 was added to the solution in an equimolar amount relative to the starting carbostyryl compound. The mixture was concentrated to dryness and the resulting residue was dissolved in 100 ml of dimethylformamide. 3.0 g of p-toluylic acid chloride was added to the solution while cooling with ice-water, and the resulting mixture was stirred for 1.5 hours at room temperature. The precipitate formed was separated by filtration, and washed successively with dimethylformamide and diethyl ether to obtain 4.2 g of 5-(1-hydroxy-2-isopropylaminobutyl)-8-p-methylbenzoyloxycarbostyril having a melting point of 197°–198° C. (after recrystallization from chloroform-diethyl ether).

EXAMPLE 13

3.28 g of 5-(1-hydroxy-2-isopropylaminobutyl)-8-hydroxy-3,4-dihydrocarbostyril hydrochloride was dissolved in 50 ml of methanol, and a 10% methanolic solution of sodium methylate was added to the solution $$B-\overset{R^4}{\underset{|}{CH}}-NHR^5$$

(structure: quinoline with $OR^1$ at 8-position and $OR^3$ at 2-position)

| Examples | $R^4$ | $R^5$ | $R^1$ | $R^3$ | B | Melting Point (°C.) |
|---|---|---|---|---|---|---|
| 7 | $C_2H_5$ | $C_2H_5$ | $-COCH(CH_3)_2$ | $-COCH(CH_3)_2$ | $-CH-$ with $OCOCH(CH_3)_2$ | 183–185 (Hydrochloride) |
| 8 | $C_2H_5$ | $C_2H_5$ | $-COCH(CH_3)_2$ | $-H$ | $-CH-$ with $OH$ | 214–216 (with coloration and decomposition) (Hydrochloride) |
| 9 | H | $-CH(CH_3)_2$ | $-COCH(CH_3)_2$ | $-H$ | $-CH-$ with $OH$ | 217–219 (with coloration and decomposition) (Hydrochloride) |
| 10 | $C_2H_5$ | $-CH(CH_3)_2$ | $-COCH_3$ | $-H$ | $-CH-$ with $OCOCH_3$ | 201–203 (Hydrochloride) |

EXAMPLE 11

5.8 g of 5-(1-hydroxy-2-isopropylaminobutyl)-8-hydroxycarbostyril was dissolved in 100 ml of methanol, and a methanolic solution of 10% sodium methylate was added to the resulting solution in an equimolar amount relative to the starting carbostyril compound. The mixture was concentrated to dryness and the resulting residue was dissolved in 100 ml of dimethylformamide. 2.9 g of cyclohexanecarboxylic acid chloride was then added while cooling with ice-water and the mixture was stirred for one hour at a temperature of 0° C. The precipitate formed was separated by filtration and washed successively with dimethylformamide and diethyl ether to obtain 4.0 g of 8-cyclohexylcarbonyloxy-5-(1-hydroxy-2-isopropylaminobutyl)carbostyril having a melting point of 186.5°–187.5° C. (after recrystallization from chloroform-diethyl ether).

EXAMPLE 12

5.8 g of 5-(1-hydroxy-2-isopropylaminobutyl)-8-hydroxycarbostyril was dissolved in 150 ml of methanol, and a 15% methanolic solution of sodium methylate was added to the solution in an equimolar amount relative to the starting carbostyryl compound. The resulting mixture was concentrated to dryness, and the residue was dissolved in dimethylformamide. 1.6 g of cyclohexanecarboxylic acid chloride was added to the solution and the mixture was stirred for 2 hours at a temperature of 10° C. The reaction mixture was poured into ice-water and the mixture was extracted with chloroform. A mixture of diethyl ether and petroleum benzene was added to the extract to obtain 1.2 g of crystalline 8-cyclohexylcarbonyloxy-5-(1-hydroxy-2-isopropylaminobutyl)-3,4-dihydrocarbostyril having a melting point of 148°–149° C. (after recrystallization from chloroform-n-hexane).

EXAMPLE 14

3.28 g of 5-(1-hydroxy-2-isopropylaminobutyl)-8-hydroxy-3,4-dihydrocarbostyril hydrochloride was dissolved in 50 ml of methanol, and a 20% methanolic solution of sodium methylate was added to the solution in an amount of 2 moles per mole of the starting carbostyryl compound. The mixture was then concentrated to dryness, and the residue was dissolved in dimethylformamide. 1.7 g of p-toluylic acid chloride was added to the solution while cooling with ice-water and the mixture was stirred for 4 hours at room temperature. The reaction mixture was poured into ice-water and extracted with chloroform. A mixture of diethyl ether and petroleum benzene was added to the chloroform extract to obtain 1.94 g of crystalline 5-(1-hydroxy-2-isopropylaminobutyl)-8-p-methylbenzoyloxy-3,4-dihydrocarbostyril having a melting point of 151.5°–152.5° C. (after recrystallization from chloroform-n-hexane).

EXAMPLE 15

1 g of 5-(1-hydroxy-2-α,α-dimethylphenethylaminoethyl)-8-hydroxycarbostyril hydrochloride was suspended in 30 ml of methanol, and a 15% methanolic solution of sodium methylate was added in an amount of 2 moles per mole of the starting carbostyril compound. The mixture was then concentrated to dryness, and the residue was dissolved in 30 ml of dimethylformamide. 0.44 g of cyclohexanecarboxylic acid chloride was then added to the solution while cooling with ice-water, and the mixture was stirred for 4 hours at room temperature. The reaction mixture was poured into ice-water and extracted with chloroform. Diethyl ether was added to the extract to obtain 0.17 g of crystalline 8-cyclohexylcarbonyloxy-5-(1-hydroxy-2-α,α-dimethylphenethylaminoethyl)carbostyril having a melting point of 158°–159° C. (after recrystallization from chloroform-n-hexane).

EXAMPLE 16

In the same manner as described in Example 15 but using the corresponding 3,4-dihydrocarbostyril starting material in place of the carbostyril starting material, 8-cyclohexylcarbonyloxy-5-(1-hydroxy-2-α,α-dimethylphenethylaminoethyl)-3,4-dihydrocarbostyril having a melting point of 146.5° to 148° C. was obtained.

EXAMPLE 17

3.36 g of 5-(1-hydroxy-2-isopropylaminobutyl)-8-hydroxycarbostyril hydrochloride was dissolved in 20 ml of trifluoroacetic acid, and 8.8 g of cyclohexanecarboxylic acid chloride was added to the solution. The mixture was then heated at a temperature of 85° C. while refluxing. The reaction mixture was concentrated and diethyl ether was added to the residue to crystallize the product. The crystals thus obtained were separated by filtration and washed with diethyl ether. The resulting crystals were extracted successively with a saturated aqueous solution of sodium bicarbonate and chloroform, and the organic layer was washed with water, dried and concentrated to dryness. The resulting residue was crystallized from a mixture of diethyl ether and petroleum benzene to obtain 3.59 g of 5-(1-cyclohexylcarbonyloxy-2-isopropylaminobutyl)-8-cyclohexylcarbonyloxycarbostyril having a melting point of 162° to 163° C. (after recrystallization from chloroform-n-hexane).

EXAMPLE 18

3.36 g of 5-(1-hydroxy-2-isopropylaminobutyl)-8-hydroxycarbostyril hydrochloride was dissolved in 20 ml of trifluoroacetic acid, and 7.75 g of p-toluylic acid chloride was added to the solution. The mixture was then heated at a temperature of 85° C. while refluxing. The reaction mixture was concentrated and diethyl ether was added to the concentrate to crystallize the product. The crystals thus obtained were separated by filtration and washed with diethyl ether. The crystals were extracted successively with a saturated aqueous solution of sodium bicarbonate and chloroform, and the organic layer was washed with water, dried and concentrated to dryness. The resulting residue was crystallized from a mixture of diethyl ether and petroleum benzene to obtain 1.14 g of 5-(1-p-methylbenzoyloxy-2-isopropylaminobutyl)-8-p-methylbenzoyloxycarbostyril having a melting point of 154°–155.5° C. (after recrystallization from chloroform-n-hexane).

EXAMPLE 19

In the same manner as described in Example 18 but using the corresponding 3,4-dihydrocarbostyril starting material in place of the carbostyril starting material, 5-(1-p-methylbenzoyloxy-2-isopropylaminobutyl)-8-p-methylbenzoyloxy-3,4-dihydrocarbostyril having a melting point of 141°–143° C. was produced.

EXAMPLE 20

3 ml of isobutyric anhydride was added to 500 mg of 8-cyclohexylcarbonyloxy-5-(1-hydroxy-2-isopropylaminobutyl)carbostyril, and the mixture was allowed to react for 1 hour at a temperature of 60° C. After completion of the reaction, 2 to 3 drops of concentrated hydrochloric acid and 5 ml of methanol were added to the reaction mixture while cooling with ice-water followed by addition of diethyl ether to crystallize the product. The crystals thus obtained were separated by filtration, washed with diethyl ether and recrystallized from a mixture of methanol and diethyl ether to obtain 480 mg of 8-cyclohexylcarbonyloxy-5-(1-isobutyryloxy-2-isopropylaminobutyl)carbostyril hydrochloride having a melting point of 214° to 215° C. (with decomposition).

EXAMPLE 21

4 g of 5-(1-hydroxy-2-isopropylaminobutyl)-8-hydroxycarbostyril hydrochloride was suspended in 20 ml of methanol, and sodium methylate prepared from 575 mg of sodium metal and 12 ml of absolute methanol was added to the suspension. The mixture was then concentrated to dryness, and the resulting residue was dissolved in 20 ml of diemthylformamide. 2.5 g of veratric acid chloride dissolved in 10 ml of dimethylformamide was then added dropwise to the mixture while cooling with ice-water. The mixture was then stirred for 1 hour, and the precipitate formed was separated by filtration, washed with diethyl ether and recrystallized from a mixture of chloroform and diethyl ether to obtain 4.3 g of 8-(3,4-dimethoxyphenylcarbonyloxy)-5-(1-hydroxy-2-isopropylaminobutyl)carbostyril having a melting point of 197°–198° C.

EXAMPLE 22

2 ml of cyclohexanecarboxylic acid and 2 ml of cyclohexanecarbonyl chloride were added to 1 g of 8-toluyloxy-5-(1-hydroxy-2-isopropylaminobutyl)carbostyril and the mixture was allowed to react for 1 hour at a temperature of 80° C. After completion of the reaction, 2 to 3 drops of concentrated hydrochloric acid and 10 ml of methanol were added to the reaction mixture while cooling with ice-water followed by addition of diethyl ether to crystallize the product. The crystals thus obtained were separated by filtration, washed with diethyl ether and recrystallized from a mixture of methanol and diethyl ether to obtain 1.3 g of 8-toluyloxy-5-

(1-cyclohexylcarbonyloxy-2-isopropylaminobutyl)carbostyril hydrochloride having a melting point of 231°–232.5° C.

EXAMPLE 23

2 ml of cyclopropanecarboxylic acid and 1 ml of cyclopropanecarboxylic acid chloride were added to 500 mg of 5-[1-hydroxy-2-(3,4-dimethoxyphenethylamino)ethyl]-8-hydroxycarbostyril hydrochloride, and the mixture was allowed to react for 1 hour at a temperature of 80° C. After completion of the reaction, 10 ml of methanol was added to the reaction mixture while cooling with ice-water followed by addition of diethyl ether to crystallize the product. The crystals thus obtained were separated by filtration, washed with diethyl ether and recrystallized from a mixture of ethanol and acetone to obtain 210 mg of 5-[1-cyclopropylcarbonyloxy-2-(3,4-dimethoxyphenethylamino)ethyl]-8-cyclopropylcarbonyloxycarbostyril hydrochloride having a melting point of 167°–168° C. (with decomposition).

EXAMPLE 24

5 g of 5-(1-hydroxy-2-ethylaminobutyl)-8-hydroxycarbostyril was suspended in 20 ml of methanol, and sodium methylate prepared from 458 mg of sodium metal and 9.6 ml of absolute methanol was added to the suspension. The mixture was then concentrated to dryness, and the resulting residue was dissolved in 30 ml of dimethylformamide. 3.3 g of $\beta$-cyclohexylpropionyl chloride was then added dropwise to the mixture while cooling with ice-water. The mixture was then stirred for 1 hour at room temperature, and diethyl ether was added to the mixture. The precipitate formed was separated by filtration, washed with diethyl ether and recrystallized from a mixture of methanol and diethyl ether to obtain 3.86 g of 8-($\beta$-cyclohexylpropionyloxy)-5-(1-hydroxy-2-ethylaminobutyl)carbostyril having a melting point of 233°–234° C. (with decomposition).

EXAMPLE 25

5 g of 5-(1-hydroxy-2-ethylaminobutyl)-8-hydroxycarbostyril was suspended in 20 ml of methanol, and sodium methylate prepared from 460 mg of sodium metal and 9.6 ml of absolute methanol was added to the suspension. The mixture was then concentrated to dryness, and the resulting residue was dissolved in 20 ml of dimethylformamide. 2.9 g of phenylacetyl chloride was then added dropwise to the mixture while cooling with ice-water. The mixture was then stirred for 1 hour at room temperature, and diethyl ether was added to the mixture. The upper layer was removed by decantation, and diethyl ether was added to the lower layer to crystallize the product. The crystals thus obtained were separated by filtration, washed with diethyl ether and recrystallized from a mixture of chloroform and diethyl ether to obtain 4.43 g of 5-(1-hydroxy-2-isopropylaminobutyl)-8-phenylacetoxycarbostyril having a melting point of 122.5°–123.5° C.

EXAMPLE 26

1 g of 5-(1-hydroxy-2-benzylaminobutyl)-8-hydroxycarbostyril hydrochloride was suspended in 20 ml of methanol, and sodium methylate prepared from 135 mg of sodium metal and 2.8 ml of absolute methanol was added to the suspension. The mixture was then concentrated to dryness, and the resulting residue was dissolved in 10 ml of dimethylformamide. 490 mg of p-chlorobenzoyl chloride was then added dropwise to the mixture while cooling with ice-water. The mixture was then stirred for 1 hour, and water was added to the mixture. The mixture was then extracted with chloroform, and chloroform was removed by distillation. Diethyl ether was added to the residue to crystallize the product, and the crystals were separated by filtration, washed with diethyl ether and recrystallized from a mixture of chloroform and diethyl ether to obtain 110 mg of 8-(p-chlorobenzoyloxy)-5-(1-hydroxy-2-benzylaminobutyl)carbostyril having a melting point of 125°–126° C.

EXAMPLE 27

1 g of 5-(1-hydroxy-2-tert-butylaminopropyl)-8-hydroxycarbostyril hydrochloride was suspended in 15 ml of methanol, and sodium methylate prepared from 155 mg of sodium metal and 3.3 ml of absolute methanol was added to the suspension. The mixture was then concentrated to dryness, and the resulting residue was dissolved in 10 ml of dimethylformamide. 593 mg of piperonylyl chloride dissolved in 5 ml of dimethylformamide was then added dropwise to the mixture while cooling with ice-water. The mixture was then stirred for 1 hour, and water was added to the mixture followed by extraction with chloroform. Chloroform was removed by distillation, and diethyl ether was added to the residue to crystallize the product. The crystals thus obtained were separated by filtration, washed with diethyl ether and recrystallized from a mixture of chloroform and diethyl ether to obtain 520 mg of 8-(3,4-methylenedioxyphenylcarbonyloxy)-5-(1-hydroxy-2-tert-butylaminopropyl)carbostyril having a melting point of 156°–157° C.

EXAMPLES 28–31

In the same manner as described in Example 1, each of the following compounds was prepared from an appropriate starting material:

8-(3,3-dimethylbutyryloxy)-5-(1-hydroxy-2-isopropylaminobutyl)carbostyril hydrochloride having a melting point of 234°–235° C. (with decomposition), 8-isobutyryloxy-5-(1-hydroxy-2-tert-butylaminopropyl)carbostyril hydrochloride having a melting point of 222°–224° C. (with decomposition), 8-(2,2-dimethylpropionyloxy)-5-(1-hydroxy-2-isopropylaminobutyl)carbostyril hydrochloride having a melting point of 257°–259°0 C. (with decomposition), 8-acetoxy-5-(1-hydroxy-2-ethylaminobutyl)carbostyril hydrochloride having a melting point of 212.5°–214° C. (with decomposition).

EXAMPLE 32

3 g of 5-(1-hydroxy-2-isopropylaminobutyl)-8-hydroxycarbostyril was added to 200 ml of anhydrous chloroform, and 3 ml of isobutyric anhydride was added dropwise to the mixture. The resulting mixture was stirred for 5 hours at room temperature, and the solvent was removed by distillation under reduced pressure. Petroleum ether was added to the residue, and the crystals formed were separated by filtration. The crystals were rendered neutral with 50 ml of a cold saturated aqueous solution of sodium bicarbonate, and insoluble material was separated by filtration and washed with water. The resulting material which was found to be a mixture of about 7 components by thin layer chromatography was then subjected to silica gel column chromatography using a silica gel of Grade C-200 (trade name of Wako Junyaku, Japan) and a mixture of chloroform and methanol (20:1 by volume) as an eluant to obtain an eluate containing four main components. The solvent was then removed by distillation from the eluate, and 5 ml of a saturated ethanolic solution of hydrogen chloride was added to the residue. Petroleum ether was added to the mixture, and the precipitated crystals were separated by filtration and recrystallized from acetone to obtain, as main components, 1.5 g of 5-(1-isobutyryloxy-2-isopropylaminobutyl)-8-isobutyryloxycarbostyril hydrochloride monohydrate having a melting point of 198°–199° C., 0.1 g of 2,8-diisobutyryloxy-5-(1-hydroxy-2-isopropylaminobutyl)-quinoline hydrochloride having a melting point of 201°–203° C. (with decomposition), 0.4 g of 5-(1-hydroxy-2-isopropylaminobutyl)-8-isobutyryloxycarbostyril hydrochloride having a melting point of 228°–229° C. (with coloration and decomposition), and 0.1 g of 2-isobutyryloxy-5-(1-hydroxy-2-isopropylaminobutyl)-8-hydroxyquinoline hydrochloride having a melting point of 225°–226.5° C. (with coloration and decomposition).

As set forth previously, the carbostyril derivatives of the present invention possess an excellent $\beta$-adrenoreceptor stimulating activity. In particular, these compounds exhibit a long-lasting and selective activity on $\beta_2$-receptor and, therefore, they are particularly useful as bronchodilators, as illustrated by pharmacological activity shown in Reference Example 4 below. In determining the activity, Salbutamol was used as a Reference Compound (1), 8-hydroxy-5-(1-hydroxy-2-ethylaminobutyl)carbostyril hydrochloride (IV) as a Comparative Compound (2) and the following test compounds (3) to (14) of the present invention:

(3) 8-acetoxy-5-(1-acetoxy-2-isopropylaminobutyl)carbostyril hydrochloride (Ib),
(4) 8-acetoxy-5-(1-hydroxy-2-ethylaminobutyl)carbostyril hydrochloride (Ia),
(5) 8-(3-cyclohexylbutyryloxy)-5-(1-hydroxy-2-ethylaminobutyl)carbostyril hydrochloride (Ia),
(6) 8-(3,3-dimethylbutanoyloxy)-5-(1-hydroxy-2-isopropylaminobutyl)carbostyril (Ia),
(7) 8-phenylacetoxy-5-(1-hydroxy-2-isopropylaminobutyl)carbostyril hydrochloride (Ia),
(8) 8-cyclopropylcarbonyloxy-5-[1-cyclopropylcarbonyloxy-2-(3,4-dimethoxyphenethylamino)ethyl]-carbostyril hydrochloride (Ib),
(9) 8-(4-methylbenzoyloxy)-5-(1-hydroxy-2-ethylaminobutyl)carbostyril hydrochloride (Ia),
(10) 2,8-diisobutyryloxy-5-(1-hydroxy-2-isopropylaminobutyl)quinoline hydrochloride (III),
(11) 8-(4-chlorobenzoyloxy)-5-(1-hydroxy-2-benzylaminobutyl)carbostyril hydrochloride (Ia),
(12) 8-(4-methylbenzoyloxy)-5-[(1-(4-methylbenzoyloxy)-2-isopropylaminobutyl]-3,4-dihydrocarbostyril hydrochloride (Ib),
(13) 8-(4-methylbenzoyloxy)-5-(1-cyclohexylcarbonyloxy-2-isopropylaminobutyl)carbostyril hydrochloride (Ib),
(14) 8-isobutyryloxy-5-(1-hydroxy-2-tert-butylaminopropyl)carbostyril (Ia).

REFERENCE EXAMPLE 4

The stimulating activity of the compounds of this invention on $\beta$-adrenoreceptor was determined as follows: Male hydrid adult dogs, weighing 10 to 15 kg, were anesthesized with sodium pentobartital administered intravenously at a level of 30 mg/kg of body weight. Each of the anesthesized dogs was secured on its back and a cannula was inserted into the trachea. Artificial respiration was conducted using a device according to the Konzett-Rössler method (Konzett H. & Rössler R., "Versuchsanordnug zu Untersuchungen an der Bronchial Moskolatur", Arch. Exp. Path., Pharmack, 195, 71–74, 27–40 (1940). The volume of the air which overflowed at the time of inhalation was measured through a pneumotachometer to determine the bronchial resistance and the values obtained were recorded on a polygraph.

In the above procedure, histamine was employed as a bronchoconstrictor at a dosage level of 10 $\mu$g/kg of body weight, and an aqueous solution containing each of the test compounds and controls shown in Table 1 below was then administered to each of the anesthesized dogs through the femoral vein at the various dosage levels as shown in Table 1 below 1 minute before the administration of the histamine. Sodium pentobartital was infused during the procedure at a dosage level of 4 mg/kg of body weight/hr using an automatic injector in order to inhibit spontaneous respiration and to maintain the anesthetic condition constant over the test period.

$ED_{50}$ values were calculated using a Dose Response curve. At the same time the pulse was measured through a transducer and the value was recorded on a polygraph. From the polygraph, the $ED_{25}$ was calculated and the results obtained are shown in Table 1 below.

The separation ratio (S.R.) was calculated by dividing the $ED_{25}$ values demonstrating pulse increase by the $ED_{50}$ values showing abatement of bronchospasm.

The persistance time was determined by administering to a subject a test compound in such a dose that a histamine-induced bronchospasm is inhibited completely (100%), in the same manner as described above and observing the persistance of the activity of the test compound with the lapse of time. The results obtained are shown in Table 2 below.

TABLE 1

Relative Potency of Various BR(Relative -Stimulants on Histamine-induced Bronchial Resistance Increase in Terms of $ED_{50}$ and on Heart Beat in Terms of $ED_{25}$ beats/min. as Compared to Isoproterenol as a Standard Compound

| Compound No. | $ED_{50}$ ($\mu$g/kg) Compound | Bronchial Resistance(BR) Isoproterenol | Relative Potency | Heart Rate (HR) $ED_{25}$ beats/min ($\mu$g/kg) Compound | Isoproterenol | Relative Potency | Separation Ratio HR(Relative Potency) BR(Relative Potency) |
|---|---|---|---|---|---|---|---|
| Salubutamol (1) | 0.52 | 0.09 | 6.1 | 2.8 | 0.061 | 45.9 | 7.52 |
| (2) | 0.66 | 0.19 | 3.47 | 3.6 | 0.09 | 40.0 | 11.5 |
| (3) | 0.82 | 0.14 | 5.85 | 4.5 | 0.07 | 64.4 | 11.0 |
| (4) | 0.61 | 0.16 | 3.81 | 3.6 | 0.08 | 45.0 | 11.8 |
| (5) | 0.67 | 0.13 | 5.15 | 6.5 | 0.10 | 65.4 | 12.7 |
| (6) | 0.42 | 0.12 | 3.52 | 3.2 | 0.07 | 46.1 | 13.1 |

TABLE 1-continued
Relative Potency of Various BR(Relative -Stimulants on Histamine-induced Bronchial Resistance Increase in Terms of $ED_{50}$ and on Heart Beat in Terms of $ED_{25}$ beats/min. as Compared to Isoproterenol as a Standard Compound

| Compound No. | $ED_{50}$ ($\mu$g/kg) Compound | Bronchial Resistance(BR) Isoproterenol | Relative Potency | Heart Rate (HR) $ED_{25}$ beats/min ($\mu$g/kg) Compound | Isoproterenol | Relative Potency | Separation Ratio HR(Relative Potency) BR(Relative Potency) |
|---|---|---|---|---|---|---|---|
| (7) | 0.17 | 0.15 | 1.13 | 1.39 | 0.11 | 12.6 | 11.2 |
| (8) | 0.51 | 0.11 | 4.64 | 4.81 | 0.07 | 68.7 | 14.8 |
| (9) | 0.16 | 0.15 | 1.06 | 1.7 | 0.11 | 15.5 | 14.5 |
| (10) | 0.95 | 0.16 | 5.94 | 5.6 | 0.10 | 56.4 | 9.5 |
| (11) | 0.91 | 0.14 | 6.50 | 4.2 | 0.09 | 46.7 | 7.2 |
| (12) | 0.73 | 0.10 | 7.30 | 8.3 | 0.11 | 75.5 | 10.3 |
| (13) | 0.71 | 0.12 | 5.92 | 6.02 | 0.09 | 66.9 | 11.3 |
| (14) | 0.47 | 0.12 | 3.92 | 3.86 | 0.08 | 48.3 | 12.3 |

As is apparent from the above results, each of the test compounds exhibits an activity which is more selective to the $\beta_2$-receptor than that of Comparative Compounds (1) and (2).

Referring now to Figure, the test compounds [Compounds (3), (4) and (10)] exhibit a long-lasting $\beta$-stimulation activity on histamine-induced bronchospasm as compared with that of the comparative compound [Compound (2)] when the compounds are tested in anesthesized dogs.

Further, the acute toxicity by intravenous administration was determined with respect to the test compounds shown in Table 2 below using 5 to 6 groups each containing 10 male rats (dd strain; body weight: 18 to 22 g) which had been fasted for 12 hours prior to the test. The $LD_{50}$ (50% lethal dose) results are as follows.

TABLE 2

| Compound | $LD_{50}$ (mg/kg, i.v.) |
|---|---|
| (3) | 112 |
| (4) | 105 |
| (6) | 107 |
| (8) | 123 |
| (9) | 132 |
| (12) | 153 |
| (13) | 147 |

The compounds of the present invention can be administered at a dosage level of from 0.1 to 50 $\mu$g/kg/day by oral, intravenous, intramuscular, intrarectal or inhalation administration.

The compounds of the present invention are advantageously administered in the form of an aerosol spray formulation by inhalation.

Typical examples of suitable formulations are given below, but it is to be noted that other dosage forms can also be prepared using other compounds of this invention according to the well-established pharmaceutical techniques.

FORMULATION 1

Tablest each containing the following components were prepared from the following components:

| Components | Amount |
|---|---|
| 8-Acetoxy-5-(1-hydroxy-2-isopropyl-aminobutyl)carbostyril | 1.2 mg |
| Corn Starch | 69.8 mg |
| Magnesium Stearate | 9 mg |
| Lactose | 20 mg |

| Components | Amount |
|---|---|
| Total | 100 mg |

FORMULATION 2

An aerosol spray for inhalation containing the following components per dose was prepared and filled into an aerosol dispenser:

| Components | Amount |
|---|---|
| 8-Acetoxy-5-(1-hydroxy-2-isopropylamino-butyl)carbostyril | 60 mcg |
| Oleic Acid | 10 mcg |
| Dichlorodifluoromethane | 57 mg |
| Trichlorofluoromethane | 25 mg |

While the invention has been described in detail and with reference to specific embodiments thereof, it will be apparent to one skilled in the art that various changes and modifications can be made therein without departing from the spirit and scope thereof.

What is claimed is:

1. A carbostyril compound represented by the formula (I):

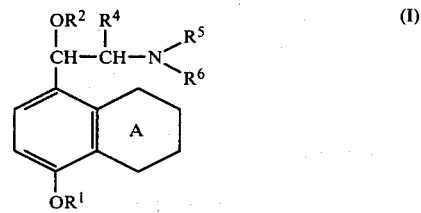

and the ring A has a partial structure:

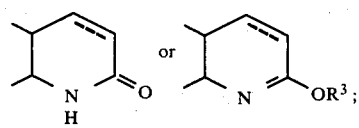

wherein $R^1$, $R^2$ and $R^3$, which may be the same or different, each represents a hydrogen atom, a cycloalkylcarbonyl group having 4 to 8 carbon atoms, a cycloalkylalkanoyl group having 3 to 7 carbon atoms in the cycloalkyl moiety and 2 to 4 carbon atoms in the alkanoyl moiety, a benzoyl group, an alkanoyl group having 2 to 6 carbon atoms or a phenylalkylcarbonyl group having 1 to 4 carbon atoms in the alkyl moiety; R⁴ represents a hydrogen atom or an alkyl group having 1 to 4 carbon atoms, R⁵ and R⁶, which may be the same or different, each represents a hydrogen atom, an alkyl group having 1 to 4 carbon atoms, a cycloalkyl group having 4 to 6 carbon atoms, or a phenylalkyl group having 1 to 4 carbon atoms in the alkyl moiety, or R⁵ and R⁶ may, when taken together with the nitrogen atom to which they are attached, form a heterocyclic ring selected from the group consisting of pyrrolidino, piperidino, morpholino and piperazino, which heterocyclic ring can be unsubstituted or substituted with an alkyl group having 1 to 4 carbon atoms; with the proviso that at least one of R¹, R² and R³ represents said cycloalkylcarbonyl group, said cycloalkylalkanoyl group, said benzoyl group, said alkanoyl group, or said phenylalkylcarbonyl group and each of R¹ and R² is not a hydrogen atom when R³ is absent; and pharmaceutically acceptable acid addition salts of said carbostyril compounds of the formula (I).

2. The carbostyril compound according to claim 1 represented by the formula (Ib):

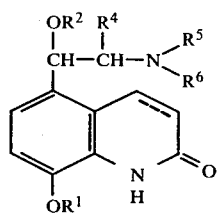

wherein R¹, R², R⁴, R⁵ and R⁶ are as defined in claim 1, and the pharmaceutically acceptable acid addition salts thereof.

3. 5-(1-Isobutyryloxy-2-isopropylaminobutyl)-8-isobutyryloxycarbostyril, according to claim 2.

4. 8-Acetoxy-5-(1-acetoxy-2-isopropylaminobutyl)-carbostyril, according to claim 2.

5. 5-(1-Cyclohexylcarbonyloxy-2-isopropylaminobutyl)-8-cyclohexylcarbonyloxycarbostyril, according to claim 2.

6. 5-(1-p-Methylbenzoyloxy-2-isopropylaminobutyl)-8-p-methylbenzoyloxycarbostyril, according to claim 2.

7. 5-(1-p-Methylbenzoyloxy-2-isopropylaminobutyl)-8-p-methylbenzoyloxy-3,4-dihydrocarbostyril, according to claim 2.

8. 8-Cyclohexylcarbonyloxy-5-(1-isobutyryloxy-2-isopropylaminobutyl)carbostyril, according to claim 2.

9. 8-Toluyloxy-5-(1-cyclohexylcarbonyloxy-2-isopropylaminobutyl)carbostyril, according to claim 2.

10. 5-[1-Cyclopropylcarbonyloxy-2-(3,4-dimethoxyphenethylamino)ethyl]-8-cyclopropylcarbonyloxycarbostyril, according to claim 2.

11. The carbostyril compound according to claim 1 represented by the formula (Ia):

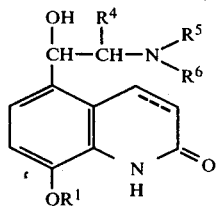

wherein R¹ represents said cycloalkylcarbonyl group, said cycloakylalkanoyl group, said benzoyl group, said alkanoyl group or said phenylalkylcarbonyl group and R⁴, R⁵ and R⁶ are as defined in claim 1, and the pharmaceutically acceptable acid addition salts thereof.

12. 5-(1-Hydroxy-2-isopropylaminobutyl)-8-isobutyryloxycarbostyril, according to claim 11.

13. 5-(1-Hydroxy-2-ethylaminobutyl)-8-acetoxycarbostyril, according to claim 11.

14. 5-(1-Hydroxy-2-tert-butylaminopropyl)-8-isobutyryloxy carbostyril, according to claim 11.

15. 5-(1-Hydroxy-2-isopropylaminobutyl)-8-isobutyryloxy-3,4-dihydrocarbosytril, according to claim 11.

16. 5-(1-Hydroxy-2-isopropylaminobutyl)-8-cyclohexylcarbonyloxycarbostyril, according to claim 11.

17. 5-(1-Hydroxy-2-isopropylaminobutyl)-8-p-methylbenzoyloxycarbostyril, according to claim 11.

18. 5-(1-Hydroxy-2-isopropylaminobutyl)-8-p-methylbenzoyloxy-3,4-dihydrocarbostyril, according to claim 11.

19. 5-(1-Hydroxy-2-α,α-dimethylphenethylaminoethyl)-8-cyclohexylcarbonyloxycarbostyril, according to claim 11.

20. 5-(1-Hydroxy-2-isopropylaminobutyl)-8-(3,4-dimethoxyphenylcarbonyloxy)carbostyril, according to claim 11.

21. 5-(1-Hydroxy-2-ethylaminobutyl)-8-(β-cyclohexylpropionyloxy)carbostyril, according to claim 11.

22. 5-(1-Hydroxy-2-isopropylaminobutyl)-8-phenylacetyloxycarbostyril, according to claim 11.

23. 5-(1-Hydroxy-2-benzylaminobutyl)-8-(p-chlorobenzoyloxy)carbostyril, according to claim 11.

24. 5-(1-Hydroxy-2-tert-butylaminopropyl)-8-(3,4-methylenedioxyphenylcarbonyloxy)carbostyril, according to claim 11.

25. 5-(1-Hydroxy-2-isopropylaminobutyl)-8-(3,3-dimethylbutyryloxy)carbostyril, according to claim 11.

26. The carbostyril compound according to claim 1 represented by the formula (Id)

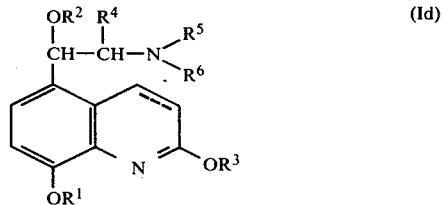

wherein R¹, R², R³, R⁴, R⁵ and R⁶ are as defined in claim 1, and the pharmaceutically acceptable acid addition salts thereof.

27. The carbostyril compound of claim 1 wherein each of R¹ and R², which may be the same or different, do not represent a hydrogen atom.

28. The carbostyril compound according to claim 2 wherein each of R¹ and R², which may be the same or different, do not represent a hydrogen atom.

29. The carbostyril compound according to claim 26 wherein R¹, R² and R³ which may be the same or different, each do not represent a hydrogen atom.

30. The carbostyril compound according to claim 1 wherein the carbon-to-carbon bonding between the 3 and 4 position of the carbostyril nucleus is a double bond, and the pharmaceutically acceptable acid addition salts thereof.

31. The carbostyril compound according to claim 26 wherein $R^4$ represents an alkyl group, and the pharmaceutically acceptable acid addition salts thereof.

32. The carbostyril compound according to claim 1 wherein $R^4$ represents a hydrogen atom, and the pharmaceutically acceptable acid addition salts thereof.

33. The carbostyril compound according to claim 1 wherein $R^1$ represents a benzoyl group, and the pharmaceutically acceptable acid addition salts thereof.

34. The carbostyril compound according to claim 1 wherein $R^1$ represents an alkanoyl group, and the pharmaceutically acceptable acid addition salts thereof.

35. The carbostyril compound according to claim 1 wherein $R^1$ represents a phenylalkylcarbonyl group, and the acid addition salts thereof.

36. The carbostyril compound according to claim 1 wherein $R^1$ represents a cycloalkylcarbonyl group, and the pharmaceutically acceptable acid addition salts thereof.

37. The carbostyril compound to claim 1 wherein $R^1$ represents a cycloalkylalkanoyl group, and the pharmaceutically acceptable acid addition salts thereof.

38. 8-(4-methylbenzoyloxy)-5-(1-hydroxy-2-ethylaminobutyl)-carbostyril, according to claim 1.

* * * * *